United States Patent [19]

Pedicano et al.

[11] Patent Number: 4,610,667
[45] Date of Patent: Sep. 9, 1986

[54] DISPOSABLE SAFETY NEEDLE SHEATH

[76] Inventors: James J. Pedicano, 222 N. Van Dien Ave., Ridgewood, N.J. 07450; James G. Kane, 3700 Oliver St., NW., Washington, D.C. 20015; Ernest Pedicano, 11 Hertford St., New Rochelle, N.Y. 10801

[21] Appl. No.: 689,909

[22] Filed: Jan. 9, 1985

Related U.S. Application Data

[63] Continuation-in-part of Ser. No. 609,343, May 11, 1984.

[51] Int. Cl.[4] ............................................. A61F 5/32
[52] U.S. Cl. .................................. 604/192; 604/263
[58] Field of Search ............... 604/192, 263; 206/365, 206/571

[56] References Cited

U.S. PATENT DOCUMENTS

| | | |
|---|---|---|
| 2,953,243 | 9/1960 | Roehr . |
| 3,021,942 | 2/1962 | Hamilton ........................ 604/192 X |
| 3,073,307 | 1/1963 | Stevens . |
| 3,074,542 | 1/1963 | Myerson . |
| 3,294,231 | 12/1966 | Vanderbeck . |
| 3,329,146 | 7/1967 | Waldman . |
| 3,333,682 | 8/1967 | Burke . |
| 3,367,488 | 2/1968 | Hamilton . |
| 3,434,473 | 3/1969 | Smith .............................. 604/192 X |
| 3,893,608 | 7/1975 | Koenig . |
| 3,934,722 | 1/1976 | Goldberg . |
| 4,113,090 | 4/1978 | Carstens . |
| 4,296,786 | 10/1981 | Brignola . |
| 4,332,323 | 6/1982 | Reenstierna . |
| 4,351,433 | 9/1982 | Elisha . |
| 4,375,849 | 3/1983 | Hanifl . |
| 4,452,358 | 6/1984 | Simpson . |
| 4,485,918 | 12/1984 | Mayer ................................. 206/366 |

FOREIGN PATENT DOCUMENTS

| | | | |
|---|---|---|---|
| 113797 | 4/1969 | Denmark ........................... | 604/192 |
| 1240228 | 3/1967 | Fed. Rep. of Germany ...... | 604/192 |

OTHER PUBLICATIONS

EPO Publication No. 160,849 for "Needle Disposal Apparatus" published Nov. 13, 1985, Theodore Karl Mayer, Rochester, N.Y.

*Primary Examiner*—John D. Yasko
*Attorney, Agent, or Firm*—Morgan & Finnegan

[57] ABSTRACT

A disposable safety needle sheath (10) has a funnel shaped receiving end (16) to protect the user's hand and guide a used needle into a sleeve (12). Retaining means (28, 30, 50, 58) engage an inserted needle and a cap (18) seals the needle sheath after the used needle has been inserted and disengaged from a syringe (36). In the preferred embodiments of the invention, the retaining means (50, 58) fixedly engage the associated needle hub structure of an inserted needle, a cap (18) is mounted by a hinge to the receiving end (16), and locking means comprised of continuous annular ridge (32) and continuous annular groove (34) is provided to prevent the cap from being opened after closing.

25 Claims, 13 Drawing Figures

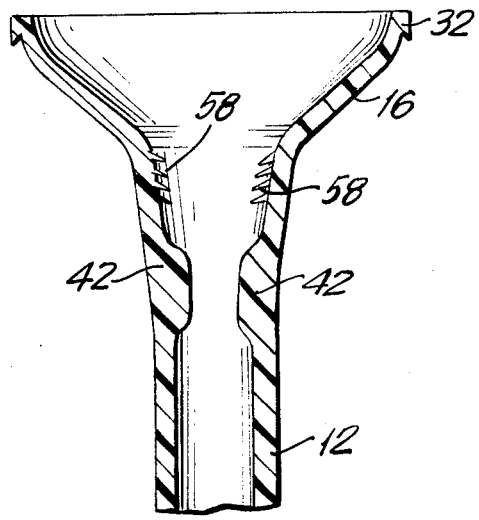
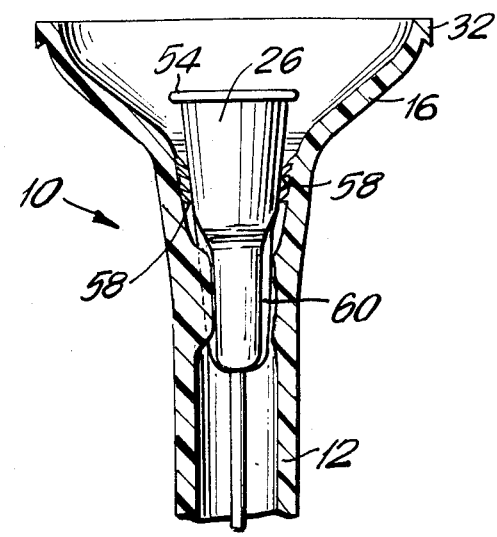
FIG.9   FIG.10
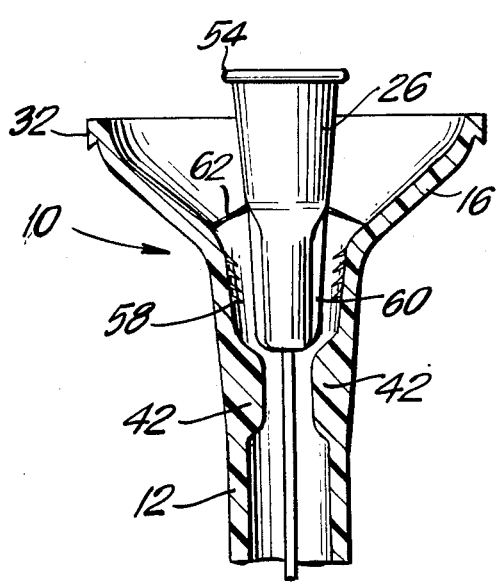
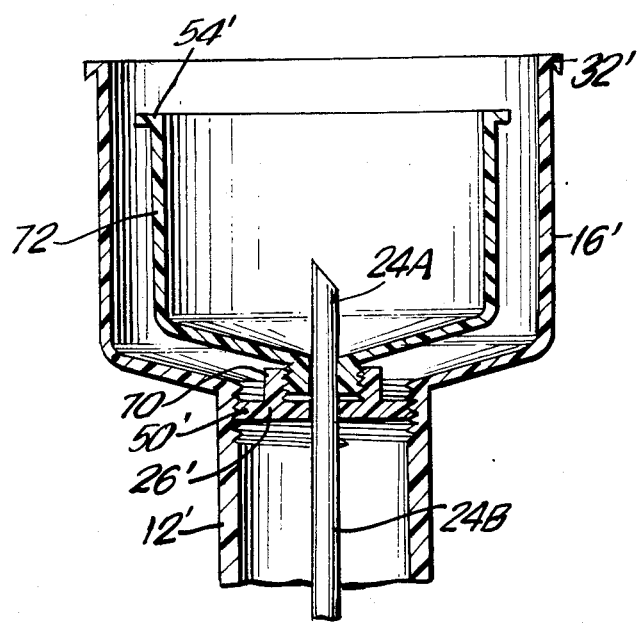
FIG.11   FIG.12

DISPOSABLE SAFETY NEEDLE SHEATH

This application is a continuation-in-part application of copending U.S. patent application Ser. No. 609,343 filed 5-11-84.

TECHNICAL FIELD

This invention relates to the safe disposal of needles and, more particularly, to a safety sheath for disposal of an unsanitary needle without danger of injury or infection.

BACKGROUND AND OBJECTS OF THE INVENTION

Infection due to contact with unsanitary medical equipment has long posed a danger to personnel handling such equipment. Contact with used medical needles is particularly hazardous since needles are characteristically very sharp objects which can cause accidental wounds.

Previous attempts to provide safety sheaths have concentrated on preserving sterility of a packaged needle prior to use and on protecting the user against injury while fastening the sterile needle to a syringe. Examples of such structures can be found in U.S. Pat. No. 2,953,243 issued to Roehr for DISPOSABLE NEEDLE ASSEMBLY; U.S. Pat. No. 3,074,542 issued to Myerson for PACKAGE FOR HYPODERMIC NEEDLES; U.S. Pat. No. 3,294,231 issued to Vanderbeck for DENTAL NEEDLE SHIELD; U.S. Pat. No. 3,367,488 issued to Hamilton for HYPODERMIC SYRINGE PACKAGE; and U.S. Pat. No. 3,329,146 issued to Waldman for NEEDLE CONTAINER. Although some of the structures disclosed in these references may also be used for disconnecting a used needle from a syringe for disposal, particularly Roehr '243, Vanderbeck '231 and Waldman '146, none of the structures disclosed provides adequate protection against injury to the hand of the user holding the sheath during reinsertion of a used needle.

Other previous attempts to provide needle sheaths which ensure sterility and provide protection against injury while fastening the needle to a syringe involve structures which must be partially destroyed to access the sterile needle. Examples of such structures, which do not provide any protection against injury or infection during disposal of the used, unsanitary needle, are found in U.S. Pat. No. 3,073,307 issued to Stevens for NEEDLE HUB AND SHEATH STRUCTURE; U.S. Pat. No. 3,333,682 issued to Burke for DISPOSABLE NEEDLE CONTAINER; and U.S. Pat. No. 3,934,722 issued to Goldberg for STERILE NEEDLE PACKAGE.

Infection even without direct contact with a used hypodermic needle also can be caused by atmospheric migration of bacteria. While some previous attempts have provided a sheath which may be used to disengage a used needle from a syringe, no structure has been provided which prevents bacteria migration. Examples of structures which allow bacteria migration after disposal of the used needle are found in U.S. Pat. No. 4,133,090 issued to Carstens for MEDICAL INSTRUMENT PACKAGE and Hamilton '488.

The only attempts to provide adequate protection against injury from direct contact with used hypodermic needles during disposal involve cannister-type containers. One such device utilizes sharp blades to sever a used needle from a syringe after it is inserted into an aperture in the cannister. Such a cannister suffers from several disadvantages. First, a cannister with blades is cumbersome and involves inconvenient transportation of the cannister itself or dangerous transportation of an exposed, used needle to the cannister. Second, the configuration of the cannister so as to contain many used needles necessarily involves a possibility that an infected needle may assume a position piercing the cannister, thereby exposing personnel handling the cannister to dangers of injury and infection by direct contact. Third, the requirement for an open aperture for inserting used needles permits undesirable bacteria migration which can also cause infection. Migration of bacteria can actually be increased by a "spray" of bacteria occurring as the sharp blades sever the infected needle.

An improved cannister for used needle disposal is disclosed in U.S. Pat. No. 4,375,849 issued to Hanifl for SYRINGE NEEDLE REMOVAL AND DISPOSAL DEVICE. This patent discloses rim guards extending from the lid of the cannister over the user's hand providing protection during insertion of a used needle, a lid opening configured for disengaging the used needle from a syringe without blades, and a closable lid to retain used needles. However, this structure also suffers from several disadvantages overcome by the present invention. While the Hanifl '849 device is described as portable, carrying the cannister to an appropriate treatment station is inconvienient since it involves handling an additional piece of equipment. Moreover, since many needles are to be disposed of in a single cannister, carrying the cannister involves risk of injury from a previously inserted needle protruding through the cannister wall. If the Hanifl '849 device is accidentally upset with the lid in the open position, i.e., while in a position to receive additional needles, previously inserted, unsanitary needles may fall out of the cannister. Reinserting such spilled needles involves direct contact with the exposed needles, thereby increasing the risk of injury. Finally, the Hanifl lid must be reopened each time another used needle is inserted, allowing potentially infectious bacteria to migrate from previously inserted needles. This last disadvantage is aggravated by the portable nature of the device since the cannister will most likely be opened in the presence of patients being treated, exposing all involved to the danger of infection from bacteria migration.

It is therefore an object of this invention to provide a new and improved safety sheath for needles.

A further object of this invention is to provide a new and improved needle safety sheath which permits control over a needle without direct contact, particularly during removal from and insertion into the sheath.

A still further object of this invention is to provide, in a new and improved needle safety sheath, means for retaining a needle in the sheath.

A still further object of this invention is to provide a new and improved needle safety sheath which permits a used needle inserted therein to be disconnected from a syringe without direct contact and which does not permit the needle to become dislodged after such disconnection from a syringe.

Another object of this invention is to provide a new and improved needle safety sheath which protects the user from injuries due to needle contact during insertion of a needle into the sheath.

A still further object of this invention is to provide, in a new and improved needle safety sheath, means for guiding a needle into a sheath sleeve during insertion.

Another object of the present invention is to provide a new and improved needle safety sheath which prevents migration of bacteria from an unsanitary needle contained therein.

Another object of the present invention is to provide a new and improved needle safety sheath which does not permit access to an unsanitary needle contained therein.

A further object of the present invention is to provide a new and improved needle safety sheath package which is tamper-proof prior to use and which does not allow access to an unsanitary needle after use.

These and other highly desirable and unusual results are accomplished by the present invention in an economical structure which may be disposed of with confidence that no injury or infection from the unsanitary needle will result.

Objects and advantages of the invention are set forth in part herein and in part will be obvious herefrom, or may be learned by practice with the invention, the same being realized and attained by means of the instrumentalities and combinations pointed out in the appended claims.

The invention consists in the novel parts, constructions, arrangements, combinations, steps, and improvements herein shown and described.

SUMMARY OF THE INVENTION

In accordance with the present invention, a disposable safety needle sheath is provided to prevent direct contact with, and secure containment for, an unsanitary needle. Means for preventing migration of infectious bacteria from the unsanitary needle are also provided.

The disposable safety needle sheath in accordance with the present invention prevents accidental contact with an unsanitary needle during insertion and urges the unsanitary needle into a durable sheath sleeve. An additional advantage of the present invention is that a needle inserted into the sleeve is frictionally engaged, allowing the needle to be disconnected from a syringe without direct contact and preventing accidental dislodging of the needle from the sleeve after the syringe has been disconnected. Means for sealing the sheath after insertion of a used needle are provided.

In a preferred embodiment of the invention a durable sleeve closed at one end and attached at the open end to the lesser diameter of a funnel-shaped receiving end is provided. The funnel-shaped receiving end protects the user's hand and urges the used needle into the sleeve during insertion of a needle into the sheath. Means for frictionally engaging and retaining a needle in the sleeve are also provided. A cap to seal the open end of the sheath having a hinge attached to the receiving end is provided. In the preferred embodiment of the invention the cap lockingly engages the receiving end when closed, making it virtually impossible to reopen the sheath without destroying both the sheath and needle.

The retaining means holds the needle within the durable narrow sleeve in a position away from the closed end of the sleeve such that the needle cannot assume a position penetrating and protruding through the sleeve. The retaining means also prevents a needle held in the sleeve from accidentally falling out of the sheath. In several alternative preferred embodiments of the invention the retaining means positively engages the needle hub, making it virtually impossible to remove a needle inserted into the sheath.

The wide aperture of the receiving end protects the user's hand gripping the sleeve during removal or insertion of a needle by overlapping and covering that portion of the hand surrounding the sleeve. The funnel shape of the receiving end surprisingly forces a sterile needle being removed from the sheath away from the user's hand holding the sheath and also guides a needle being inserted toward the narrow sleeve aperture. The receiving end may be configured and dimensioned to accomodate needle devices of varying construction, including double-ended needles having specially designed needle housings.

The cap seals the open end of the sheath to prevent bacteria migration and to provide further protection against the possibility of a needle falling out or being removed.

In the preferred embodiment of the invention the locking cap effectively prevents all access to the used needle. After closing, access can only be gained by compromising the structural integrity of the sheath. However, the sheath is constructed of durable materials which make it virtually impossible to compromise the sheath without also impairing the structure of a needle contained therein.

The hinge prevents the cap from being misplaced with respect to the other sheath components.

In use, the sheath may be sealed within a tamper-proof package with a sterile needle held therein by the retaining means and, unusually, with the locking cap in an open position. The tamper-proof package is opened and the tip of a syringe inserted into the open end of the sheath to access the needle. Of course, a syringe could alternatively be provided in a package with the sheath and sterile needle. The syringe rotationally mates with the needle hub and is removed with the needle mounted thereon by a lateral pulling action. During this removal the funnel shape of the receiving end guides the needle tip away from the hand gripping the sleeve, thereby preventing accidental injury during removal. After use the needle is inserted into the sheath while still mounted on the syringe. The wide aperture of the receiving end prevents accidental pricking of the hand and the funnel shape guides the needle into the sheath sleeve. Thus, the funnel shape of the receiving end surprisingly protects the user's hand during both removal and insertion of the needle. The inserted needle engages the retaining means and the syringe is disengaged for separate disposal. The frictional engagement of the needle with the retaining means prevents the needle from falling out of the sleeve prior to closing the cap. Closing the cap seals the sheath to prevent migration of bacteria from the used needle through the atmosphere.

In the alternative preferred embodiments of the invention wherein the retaining means positively engages the needle hub a used needle is inserted into the sheath by an axial pushing action or, alternatively, by rotational engagement of the retaining means with the needle hub. Once so inserted, a counterclockwise turning motion may be applied to disengage the syringe from the needle hub. Such embodiments are remarkably effective in preventing an inserted needle from thereafter being removed by applying either a pulling or reverse rotational force to the needle hub. Furthermore, such embodiments are surprisingly economical to construct and simple to use.

In the preferred embodiment wherein the cap locks and cannot be reopened without compromising the structure of both the sheath and needle, the surprising result of denying all access to the used needle is obtained. Thus, the sheath cannot accidentally open to allow bacteria to migrate or to allow the needle to fall out. Moreover, in those embodiments where the retaining means positively engages the needle hub the retaining means prevents the needle from falling out or being intentionally or accidentally removed by re-attaching a syringe, even if the sheath was reopened. The locked cap obtains the remarkable result of denying access to those who seek entry, whether it be medical personnel who mistakenly believe that a sterile needle is contained therein or drug abusers seeking intact needles regardless of sterility. Thus sealed, the sheath can be disposed of with confidence that the used needle contained therein presents no danger to anyone.

It will be apparent from the foregoing general description that the objects of the invention specifically enumerated herein are accomplished by the invention as here embodied.

Thus, as one advantage of the present invention, a needle may be advantageously removed from and inserted into a needle safety sheath with no direct needle contact, resulting in surprising confidence that no needle injury will result.

As a further advantage of the present invention an unsanitary needle may be inserted into a needle sheath such that the inserted needle may not, thereafter, be readily removed.

As yet a further advantage of the present invention, bacteria from the unsanitary needle is prevented from migrating through the atmosphere.

As yet a further advantage of the present invention all access to the interior of the safety sheath is effectively denied once the cap is sealed. This unexpected denial of access to the sheath may be combined with the attributes of a tamper-proof package to achieve the remarkable combination of assuring sterility of the needle prior to use and effectively preventing injury and infection before, during and after use.

It will be understood that the foregoing general description and the following detailed description as well are exemplary and explanatory of the invention but are not restrictive thereof.

BRIEF DESCRIPTION OF THE DRAWINGS

The accompanying drawings, referred to herein and constituting a part hereof, illustrate preferred embodiments of the product of the present invention, and together with the description serve to explain the principles of the invention, in which:

FIG. 9 is a partial axial cross-section view of a needle sheath constructed in accordance with the fourth preferred embodiment of the invention;

FIG. 10 is a partial axial cross-section view of the sheath structure of FIG. 9, and also illustrating a needle disposed therein;

FIG. 11 is a partial axial cross-section view of the sheath structure of FIG. 9, and also illustrating a sterile needle accessibly mounted therein; and FIG. 12 is a partial axial cross-section view of a needle sheath constructed in accordance with the present invention and configured to accomodate a double-ended needle and housing.

DESCRIPTION OF THE PREFERRED EMBODIMENTS

Figure 1:
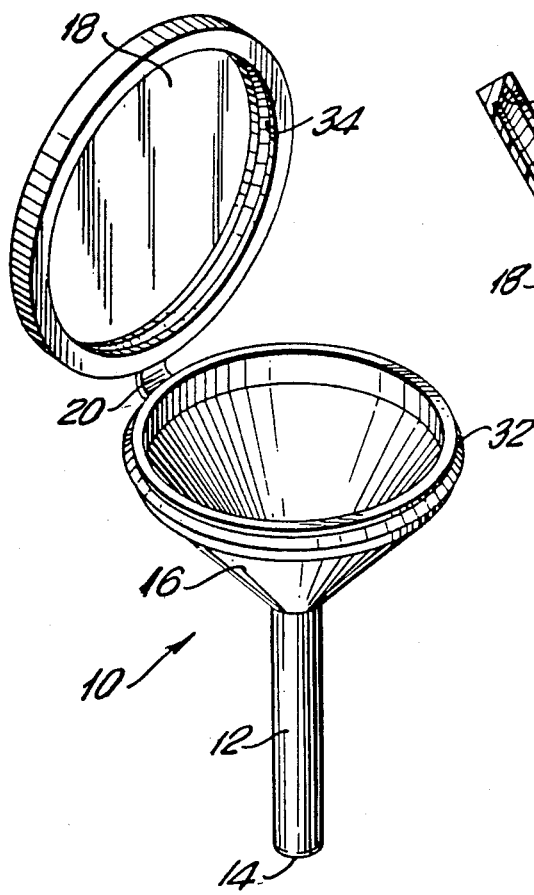
FIG. 1 is a perspective view of a disposable safety needle sheath constructed in accordance with the first preferred embodiment of the invention with the cap in an open position.

Referring now more particularly to FIGS. 1–4 of the accompanying drawings, there is illustrated a first preferred embodiment of a safety sheath constructed in accordance with the present invention, indicated generally by reference numeral 10. As here embodied, sheath 10 includes a stiff, durable sleeve 12 having a closed end 14 and an opposite open end integral with the small open end of a funnel-shaped receiving guide 16. A hinge 20 connects the receiving guide to a cap 18 for sealing the open end of sheath 10.

Sleeve 12, including the open end thereof, and the small open end of funnel-shaped receiving guide 16 are dimensioned to receive a longitudinally inserted needle and are, typically, on the order of one-eighth to one-quarter of one inch in diameter. Retention of the needle within the sleeve is obtained by frictional engagement of the needle with a narrower sleeve diameter provided by frictional surfaces 30, or by engagement of a tapered needle hub 26 with the open end of the sleeve. Rotational movement of the inserted needle relative to the sleeve is prevented by the engagement of inward flanges 42 in sleeve 12 with the outward flanges which are commonly provided on needle hubs.

The wide aperture of funnel shaped receiving guide 16 is sufficiently large to provide a large target for insertion of a needle and to cover the user's fingers gripping sleeve 12. The diameter of the wide aperture is preferably greater than one inch in order to provide a sufficiently large protective target for insertion and may be as large as three inches in order to fully cover the user's hand. The added protection of a diameter greater than three inches is minimal in relation to the inconvenience in handling such a large aperture sheath. Preferably, the wide aperture is at least twice the diameter the syringe tip which engages the needle hub (See FIG. 2).

The configuration of funnel shaped receiving guide 16 is such that a needle inserted within the wide aperture of receiving guide 16 is urged by the pitch of the funnel shape towards the small open end of the receiving guide into sleeve 12. The pitch of the funnel shape must be balanced against the convenience in handling the sheath, which makes minimizing the funnel height necessary to reach the chosen wide aperture desirable. It has been found that funnel shapes with interior angles of 80 to 140 degrees provide an adequate balance of the height to width, with interior funnel angles of 100 to 120 degrees providing desirable funnel pitch at acceptable funnel heights.

A cap 18 for sealing the open end of sheath 10 is attached to receiving guide 16 by a hinge 20. Cap 18 and receiving guide 16 are provided with locking means to prevent the sheath from being reopened after a used needle is inserted and the cap closed. As here embodied, the receiving guide is provided with a stiff annular ridge 32 to engage a recess or groove 34 on cap 18. The lip of cap 18 distorts slightly as the cap is forced over the upper slanted surface of annular ridge 32. Distortion of the cap lip results from either the use of a less rigid material than the annular ridge to form the cap lip or from the inherently weaker structure of the cap lip caused by the presence of the groove. The resilient cap resumes its natural position once the groove fully engages the annular ridge so that the flat, lower surfaces of annular ridge 32 and groove 34 come into a face to face relationship when the cap is fully closed. This facing relationship of the flat surfaces of the annular ridge and groove locks the cap in the fully closed position so it cannot easily be removed. The face to face relationship of these lower flat surfaces locks the cap closed since application of an upward force relative to said sheath merely presses these surfaces closer together, preventing the closed cap from opening. Preferably, the plane formed by the face to face flat surfaces is perpendicular to the axis of the sleeve, but at the very least the flat lower surface of annular ridge 32 must not be slanted so that upward force on cap 18 causes the same type of resilient distortion as occurs while the cap is forced closed over the upper slanted edge of annular ridge 32. As thus constructed the sheath, once closed, is tamper-proof and cannot readily be opened without the use of an external tool.

Advantageously sleeve 12, receiving guide 16, and cap 18 are all made of a stiff, lightweight material which is sufficiently rigid to prevent accidental piercing with a needle and to make improper opening after engagement of the locking closure virtually impossible. Preferably, all of these surfaces are made of a stiff durable polypropylene, high density polyethylene, acrylic, polystyrene or polyester or copolymer thereof, or any other stiff material which is substantially impermeable to penetration by a needle. Hinge 20 may be made of any material which is sufficiently flexible to allow cap 18 to move freely relative to the receiving guide without becoming disconnected therefrom.

Figure 3:
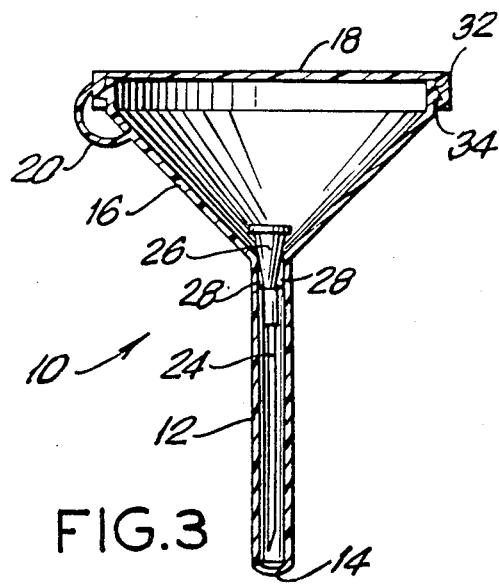
FIG. 3 is an axial, cross-section elevation view of the sheath structure of FIG. 1, and illustrating a used needle disposed in the sheath and the cap in the closed, locked postion.
Figure 4:
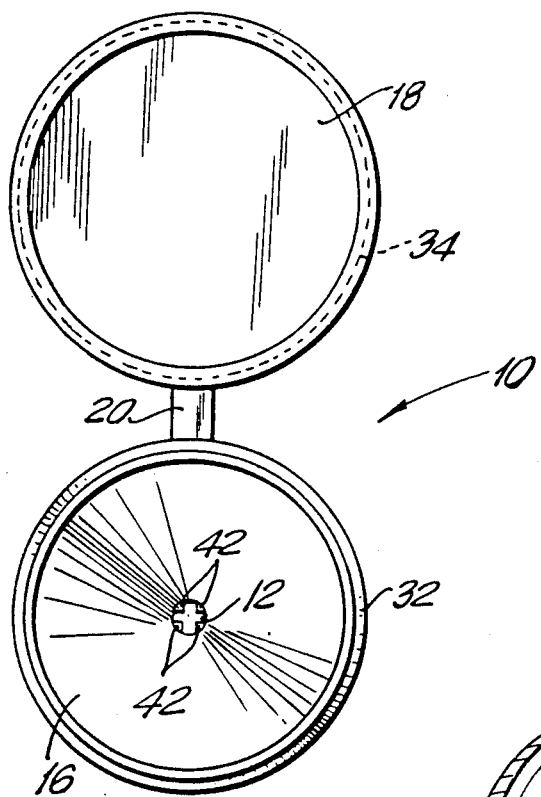
FIG. 4 is a top plan view of the sheath structure of FIG. 1.
Figure 5:
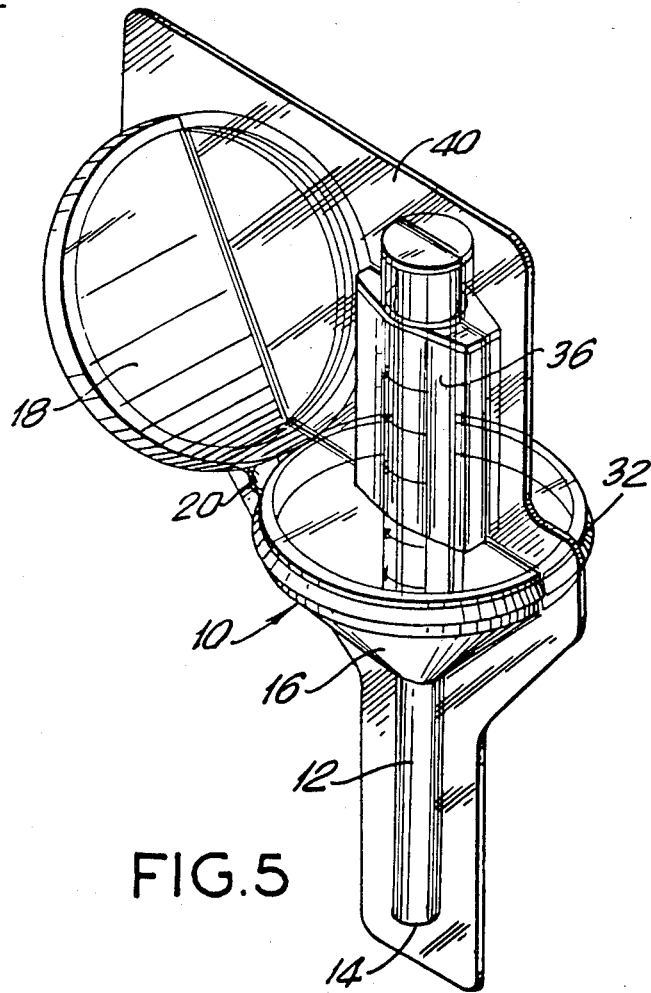
FIG. 5 is a perspective view of the second preferred embodiment of the invention disposed in a tamper-proof package as part of a kit including a sterile hypodermic needle and syringe.

In a second preferred embodiment of a safety sheath constructed in accordance with the present invention and shown in FIG. 5 with reference numerals common to FIGS. 1-4, a sterile needle is prepackaged and frictionally held in the sleeve with the cap in the open position, all sealed in a tamper-proof package. FIG. 5 shows an optional syringe 36 prepackaged with sheath 10 attached to the sterile needle. The tamper-proof package is a vacuum sealed envelope 40 of suitable flexible sheet wrapping such as cellophane, foil or plastic wrap which preserves sterility and allows determination of whether the sterility of the contents has been compromised by visual inspection. The tamper-proof package is opened to access the sterile needle and optional syringe for use. The used needle is reinserted into the sheath, disconnected from the syringe, and sealed in the sheath by closing the locking cap.

Figure 6:
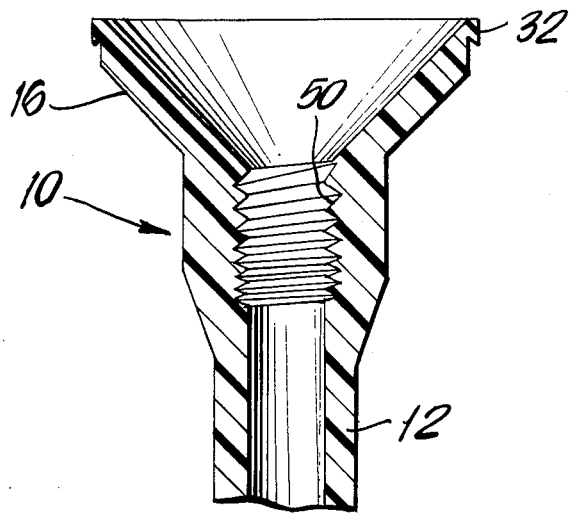
FIG. 6 is a partial axial cross-section view of a needle sheath constructed in accordance with the third preferred embodiment of the invention.
Figure 6A:
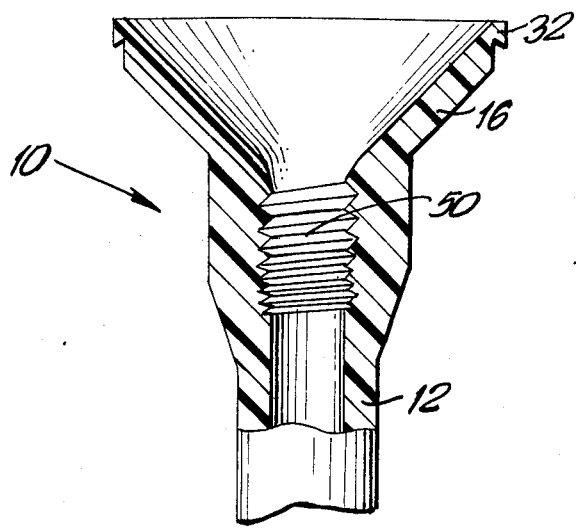
FIG. 6A is a partial elevation view of the sheath structure shown in FIG. 6, showing variation in thread spacing and pitch.
Figure 7:
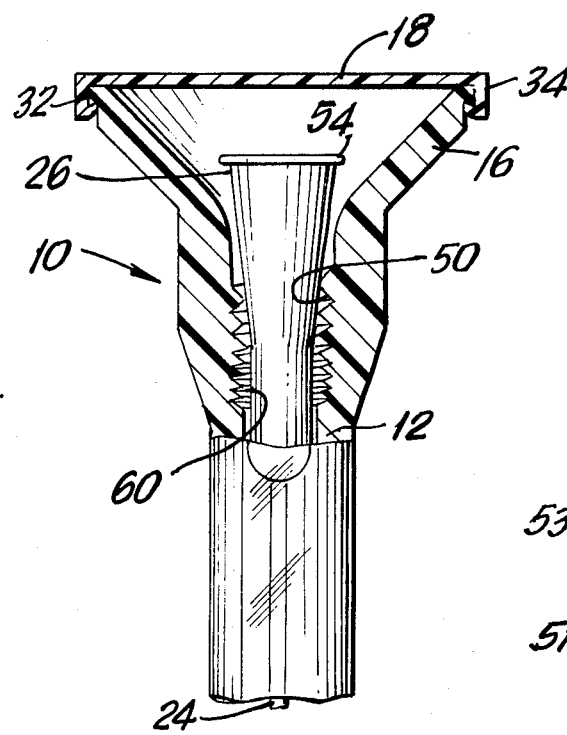
FIG. 7 is a partial axial cross-section view of the sheath structure of FIG. 6, and also illustrating a needle disposed therein and a locking cap engaged therewith.
Figure 8:
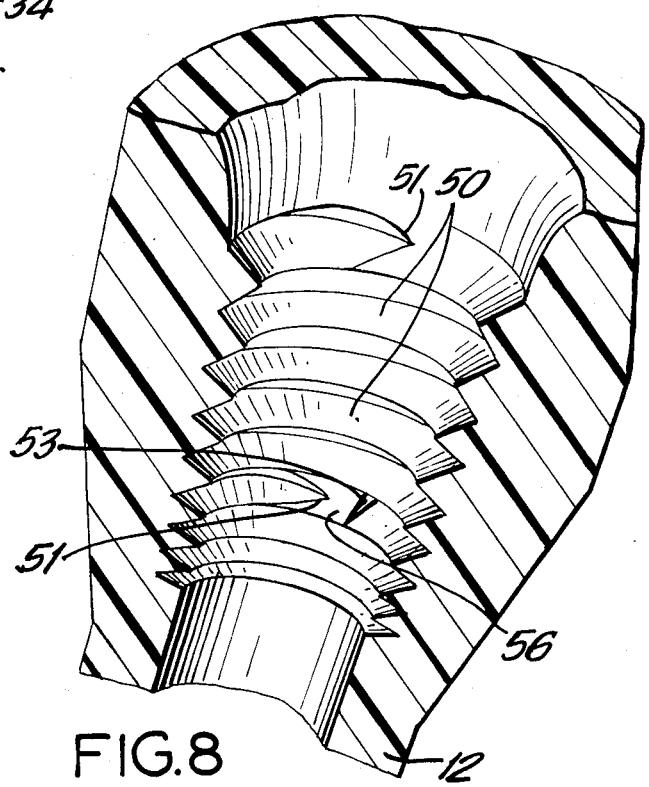
FIG. 8 is a partial cut-away perspective view of the sheath structure according to the third preferred embodiment, and also illustrating the arrangement of self-cutting needle locking threads with a gap provided therein.

A third preferred embodiment of the invention is shown in FIGS. 6-8, having reference numerals corresponding to FIGS. 1-4. As shown in FIGS. 6 and 6A, sleeve 12 is provided with needle locking threads 50. Needle locking threads 50 are formed of stiff polypropylene, high density polyethylene, acrylic, or any other relatively hard, durable material. As shown in FIG. 6, threads 50 may be relatively constant in slope or pitch and thread spacing throughout their length. Alternatively and as shown in FIG. 6A, threads 50 may be openly spaced with a steep slope near the open end of sleeve 12 and gradually decrease in slope and become more tightly spaced distal to the open end of sleeve 12. The steeply pitched threads gradually rise from a negligible thread height near the open end of the sleeve to a full thread height to provide a self-cutting action with respect to the associated structure of a needle inserted therein, i.e., the needle hub or outward needle hub flanges thereon. As clockwise rotational force is applied to the needle hub relative to the sheath via a syringe the openly spaced, steeply-pitched threads commence self-cutting threaded engagement with the outward needle hub flanges 60 provided along some or all of the tapered surface of commercially available needle hubs. Alternatively, threads 50 may engage the needle hub 26 itself rather than outward flanges 60. As further clockwise rotation occurs between the needle hub and the sheath the needle hub further engages threads 50 and is drawn into sleeve 12 until full engagement therebetween has occurred.

As shown in FIG. 7, the fully inserted needle tightly engages threads 50, particularly in the region of tightly spaced threads distal to the open end of sleeve 12. Since conventional syringe and needle hub engagement involves clockwise engagement of one or two openly spaced threads on the syringe with annular lip 54, application of sufficient clockwise rotational force relative to the sheath to tighten the associated needle structure, i.e., needle hub 26 or outward flanges 60, into threads 50 may be applied without affecting the attachment of the needle hub to the syringe. Once the needle hub has been tightened into the sleeve, however, the relatively slight counter-clockwise force required to disengage the syringe from the needle hub is readily achieved without affecting the engagement of the inserted needle with locking threads 50. Thus, sufficient counterclockwise force to disengage the needle from threads 50 cannot be created without first causing the needle hub to become disengaged from the syringe.

As shown in FIG. 8, to further prevent disengagement of an inserted needle hub 26 from sleeve 12 threads 50 may be provided with one or more thread gaps 56. The threads may be of continuously steep pitch or commence with a steep pitch and gradually decrease to a lesser, constant pitch. As previously pointed out in describing the openly spaced, steeply pitched threads, a self-cutting action with respect to the associated structure of a needle is acheived by gradual progression of the rigid thread to maximum thread height. Thread gaps 56 are created by abruptly dropping the thread height to a minimal or zero value at 53 and, after a short interval, recommencing the gradual progression at 51 back to full thread height. Outward flanges 60 are sufficiently resilient to resume substantially all of their natural shape within thread gaps 56 so that the thread gaps prevent removal of the inserted needle hub by causing crossthreading if any counter-clockwise rotational force is applied to needle hub 26 relative to sleeve 12. Furthermore, during counter-clockwise rotation the abruptly-ending threads at 53 are not capable of creating a self-cutting action such as that provided during clockwise rotational insertion of the needle hub by the open, steep-sloped threads which gradually rise to full thread height.

Thus, as needle hub 26 is inserted into sleeve 12 with a clockwise rotational force the steeply-pitched threads near the open end of the sleeve cut into outward needle hub flanges 60. As further clockwise rotational force is applied flanges 60 further engage threads 50 until tightly held within sleeve 12. During insertion flanges 60 have at least partially returned to their natural shape at one or more thread breaks 56 and re-cut thereafter so that removal by counterclockwise rotation is prevented. After insertion of the used needle is complete, application of counter-clockwise rotational force merely disconnects the syringe from needle hub 26 and does not result in removal of the inserted needle.

In either threaded arrangement according to the third preferred embodiment and heretofore discussed threads 50 are in sufficiently tight engagement with outward flanges 60 or needle hub 26 that application of a large clockwise force to the needle hub 26 via the syringe does not allow removal of the inserted needle. The gripping force of threads 50 on the associated needle structure of an inserted needle is such that, should a large clockwise force be applied to the syringe the coupling between the annular lip 54 and the tip of the syringe will fail before appreciably affecting the grip of threads 50 on the associated needle structure. This is due to the fact that the tip of the syringe is made of a more pliable polyethylene than the stiff needle sheath 10 such that annular lip 54 overrides the few threads engaged on the syringe tip before sufficient clockwise force can be created to strip needle locking threads 50. This relationship ensures that the present invention is essentially "fail safe", in that, as overtightening of the needle hub occurs the syringe merely becomes disconnected and threads 50 cannot be overpowered or become stripped.

A fourth preferred embodiment of the invention is shown in FIGS. 9 and 10, having reference numerals corresponding to FIGS. 1-8. In this embodiment gripping arms 58 are provided inside sleeve 12 near the open end thereof. Gripping arms 58 extend from the interior wall of sleeve 12 toward the axis of the sleeve and are slightly inclined toward the closed end of sleeve 12 in their rest state. Gripping arms 58 are preferably molded from stiff polypropylene, high density polyethylene, acrylic or any other relatively stiff material and may comprise pinlike protrusions or continuous ridges around all or part of the inner circumference of sleeve 12. Gripping pins 58 are sufficiently resilient to be slightly pushed aside as a needle hub is forced into the sleeve by an axial pushing motion. This axial motion slides the needle hub across the gripping arms until fully inserted into the sheath, as shown in FIG. 10. The inserted needle cannot thereafter be removed from sleeve 12 since any pulling action exerted on the needle hub causes gripping arms 58 to flex toward their rest position, effectively creating inward gripping pressure on the needle hub. The amount of inward force exerted on the needle hub is directly proportional to the pulling force exerted on the needle hub, so as greater pulling force is exerted on the needle hub the inward gripping force increases. It may also be desirable to provide sharpened tips on gripping arms 58 which actually dig into needle hub 26 as any pulling force is applied to try to remove the inserted needle from the sheath. It is further contemplated that the needle hub could be provided with ridges to engage gripping arms 58 in a ratchet-like manner as the needle is forced into the sheath.

In this embodiment it is desirable to further provide inward flanges 42, as illustrated in FIGS. 4 and 10, such that outward needle hub flanges 60 of a needle inserted into the sheath engage inward flanges 42 to facilitate disconnection of the syringe from annular lip 54. The slight rotational force necessary to engage inward flanges 42 with outward flanges 60 is minimally affected, if at all, by gripping arms 58, which only immobilize needle hub 26 when a pulling force is exerted thereon.

Either of the third or fourth preferred embodiments of the present invention may also be provided with a cap to engage annular ridge 32, as shown in FIG. 7. Since threads 50 or, alternatively, gripping arms 58 securely lock the inserted needle within sleeve 12 the cap is not necessary to prevent the needle from accidentally or intentionally becoming disconnected from sheath 10. However, a cap is nonetheless desirable in these embodiments to completely prevent access to the needle and to further prevent migration of infectious bacteria. Such a cap may also be provided with a hinge attaching the cap to the sheath.

In the third and fourth preferred embodiments heretofore discussed the sheath may be provided with break-away tab connectors 62 between needle hub 26 of a sterile needle and sheath 10, as shown in FIG. 11 with reference numerals corresponding to FIGS. 1-10. Break-away connectors 62 hold needle hub 26 of the sterile needle poised just above the securing mechanism positioned immediately within sleeve 12, shown in FIG. 11 as gripping arms 58 of the fourth preferred embodiment of the invention. Preferably, the sterile sheath and needle are sealed within a tamper-proof package such as that shown in FIG. 5, and may include a sterile syringe pre-connected to needle hub 26. Alternatively, the sterile needle and sheath may be independently sealed in a tamper-proof package to be connected to a syringe after the needle and sheath package is opened. In either case, the syringe engages annular lip 54 in a clockwise rotational motion without breaking connectors 62. Once the syringe is connected to needle hub 26 the syringe and attached needle are disconnected from sheath 10 by applying sufficient clockwise twisting and pulling motion to compromise break-away connectors 62. Thereafter, sheath 10 is available for insertion and containment of the used needle immediately after use.

The disposable needle sheath of the present invention may also be adapted for particular applications. By way of example only, the configuration of the wide-aperture receiving guide 16 may be varied to accomodate double-ended needle devices, as illustrated in FIG. 12. A double-ended needle having upper and lower needle sections 24A and 24B is fixedly attached to a needle hub 26'. Needle hub 26' has a threaded coupling 70 adapted to engage upper needle housing 72, as shown. Such a configuration of double-ended needle, needle hub, and upper needle housing is commercially available for drawing multiple vials of blood from patients wherein needle section 24B is inserted into the patient and blood is drawn from needle section 24A. Alternatively, multiple injections may be administered through needle sections 24A and 24B. In either case, needle section 24B is withdrawn from the patient while attached to upper needle housing 72 and must be disposed of.

As shown in FIG. 12, receiving guide 16' is configured to received the double-ended needle while attached to upper needle housing 26'. Needle section 24B is inserted into sleeve 12' and needle hub 26' is rotationally engaged with threads 50' in a manner similar to that previously discussed in relation to the third preferred embodiment. Receiving guide 16' may be configured to receive the entire upper needle housing as shown or may allow the top of the upper needle housing to protrude from receiving guide 16'. However, receiving guide 16' should completely enclose upper needle section 24A, as shown. If receiving guide 16' is configured to receive the entire upper needle housing a cap may be engaged with annular ridge 32' for complete containment. Alternatively, upper needle housing 72 may be disengaged from threaded coupling 70 on needle hub 26' for separate disposal in a manner similar to disengagement of a syringe according to the third preferred embodiment of the invention. Needle sections 24A and 24B remain attached to needle hub 26', which is securely held by locking threads 50'. A cap should be applied to receiving guide 16' and locked in place by engagement with annular ridge 32' in order to assure complete isolation and containment of the double-ended needle.

FIG. 1 illustrates a safety needle sheath 10 constructed in accordance with the invention having sleeve 12 with closed end 14 and an opposite open end attached to the small open end of funnel shaped receiving guide 16. The wide aperture of receiving guide 16 is distal to sleeve 12 and is configured as discussed above to cover and protect fingers gripping sleeve 12. Cap 18 is shown connected to receiving guide 16 via living hinge 20. Hinge 20 is preferably formed to position the cap ready for use and to allow closing in a simple, one-handed fashion.

Figure 2:
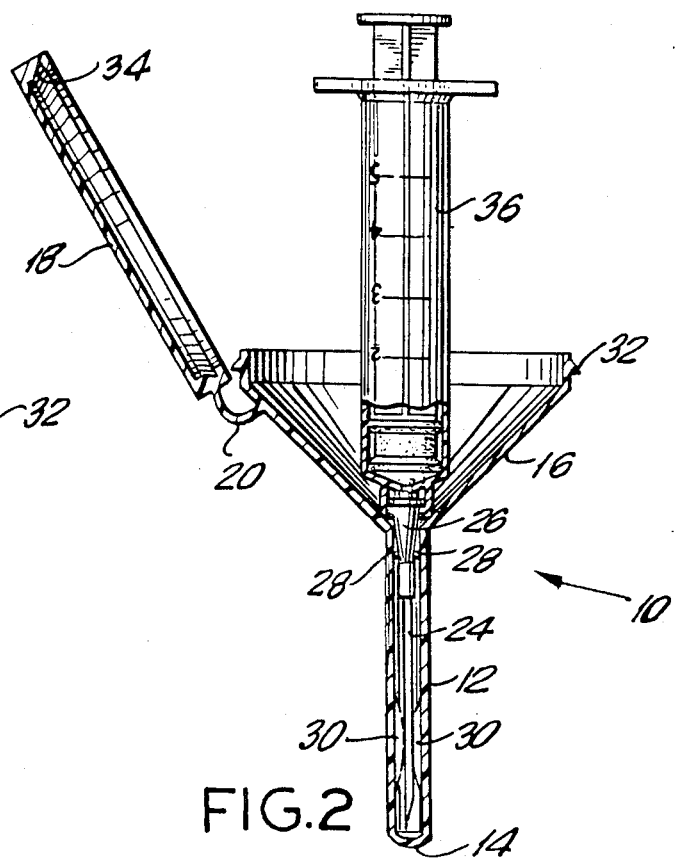
FIG. 2 is an axial, cross-section elevation view of the sheath structure of FIG. 1, and also illustrating a needle attached to a syringe inserted in the sheath and frictionally held both along the shaft of the needle and at the needle hub.

FIG. 2 is an axial cross-section view of the preferred embodiment of the invention, showing sheath 10 with a needle 24 attached to a syringe 36. The position shown in FIG. 2 can occur prior to removal of a sterile needle and syringe from the sheath or after insertion of a used needle into the sheath but prior to disconnection of the syringe from the needle. The interaction of inward flanges 42 (See FIG. 4) and protrusions on needle hub 26 (not shown) prevent rotation of the needle relative to the sheath and permit rotation of syringe 36 relative to needle hub 26 to disengage the needle from the syringe. Needle 24 is lodged in sleeve 12 by the frictional engagement of the tapered needle hub 26 with shoulders 28 at the open end of sleeve 12 or, alternatively, by engagement of needle 24 with the tapered, frictional surfaces 30 (shown by broken lines) which create a narrow sleeve diameter relative to the needle. The frictional engagement of needle 24 with frictional surfaces 30 or of tapered needle hub 26 with shoulders 28 holds the needle securely in the sleeve after the syringe is disconnected for separate disposal. The needle so held does not contact closed end 14 of sleeve 12. Cap 18 is shown in the open, unlocked position attached to receiving guide 16 by hinge 20. Sleeve 12, receiving guide 16, and shoulders 28 or, alternatively, frictional surfaces 30 are preferably formed as a single unit. Hinge 20 can also be formed as part of the single unit to provide a sheath which is a single integral body.

FIG. 3 shows the preferred embodiment of the invention with needle hub 26 frictionally engaging shoulders 28 to firmly hold needle 24 within sleeve 12. Cap 18 is in the closed, locking position with annular ridge 32 on receiving guide 16 engaging the corresponding recess or groove 34 in cap 18. Annular ridge 32 and groove 34 are shown in exaggerated detail in the figures to illustrate their interaction. As previously discussed and shown in FIG. 3, cap 18 mounts over the wide aperture of receiving guide 16 with the flat, lower surfaces of the annular ridge and groove assuming a face to face relationship, effectively preventing the cap from being reopened. Upward pressure on the cap relative to the receiving guide merely forces the flat surfaces of the annular ridge and groove more closely against one another and will not open the sheath.

FIG. 4 is a top plan view of sheath 10 illustrating the relationship between receiving guide 16 and sleeve 12, showing cap 18 in a fully open position adjacent to receiving guide 16. Annular ridge 32 and groove 34 are preferably continuous around the rims of receiving guide 16 and cap 18, respectively, as shown. Inwardly extending flanges 42 engage corresponding ridges on needle hub 26, as discussed above in relation to FIG. 2, to provide counter-rotational force during connection and disconnection of the syringe from the needle. This manner of engaging a syringe and needle is currently available in products from Becton Dickinson and Company.

FIG. 5 shows sheath 10 in a second preferred embodiment sealed within a tamper-proof sterile package 40 as part of a kit including a hypodermic syringe 36 and needle (not visible) positioned in the sheath in a manner similar to that shown in FIG. 2. In FIG. 5 sheath 10 is shown sealed in sterile envelope 40 with locking cap 18 in the open position. Tamper-proof envelope 40 preserves the sterility of the needle frictionally held in sleeve 12 and also of the optional hypodermic syringe attached to the needle hub.

FIG. 6 is a partial axial cross-section view of a needle sheath constructed in accordance with the third preferred embodiment of the invention, showing sleeve 12 having needle locking threads 50 adjacent to receiving guide 16. Needle locking threads 50 are openly spaced with a steep slope or pitch near receiving guide 16. The slope or pitch of the threads is shown as being relatively constant throughout their length. Receiving guide 16 is shown having annular ridge 32 to engage a locking cap.

FIG. 6A is a partial axial cross-section view of the needle sheath structure shown in FIG. 6, illustrating the preferred construction of needle locking threads 50. Threads 50 desirably commence with openly spaced, steeply pitched threads at the juncture of receiving guide 16 and the open end of sleeve 12. The slope or pitch of threads 50 gradually decreases and the threads gradually become closely spaced within sleeve 12 distal to receiving guide 15.

FIG. 7 is a partial axial cross-section view of the needle sheath structure of FIG. 6, and also showing a needle disposed therein. Needle 24 is shown positioned within sleeve 12. Outward flanges 60 on needle hub 26 are shown fully engaged with and secured by needle locking threads 50. Needle hub 26 is situated within the open end of sleeve 12 and receiving guide 16, with annular lip 54 disconnected from a syringe. A cap 18 effectively seals the sheath with groove 34 engaged with annular ridge 32 to provide ultimate containment.

FIG. 8 is a cut-away perspective view of a needle sheath constructed in accordance with the present invention, showing self-cutting threads 50 commencing at a negligible thread height at thread initiating points 51 and gradually increasing to full thread height. Threads 50 are preferably provided with one or more thread gaps 56 having an abrupt end point 53 followed by a non-threaded interval and a subsequent gradual increase to full thread height from a thread initiation point 51.

FIG. 9 is a partial axial cross-section view of a needle sheath constructed in accordance with the fourth preferred embodiment of the invention. Needle hub gripping arms 58 are provided within sleeve 12 near the juncture of sleeve 12 and receiving guide 16. Gripping arms 58 protrude from the inner walls of sleeve 12 toward the sleeve axis and are inclined slightly toward the closed end of sleeve 12 and away from receiving guide 16. Gripping arms 58 may be individual finger-like pins or may be continuous ridges around all or part of the inner circumference of sleeve 12. Gripping arms 58 may be desirably formed with sharpened tips distal to the inner sleeve wall. Inward flanges 42 are provided on the inner wall of sleeve 12, preferable within sleeve 12 toward closed end 14 in relation to gripping arms 58. Receiving guide 16 is provided with annular ridge 32 adapted to engage a locking cap.

FIG. 10 is a partial axial cross-section view of the needle sheath structure of FIG. 9, illustrating a needle locked securely therein. Gripping arms 58 frictionally engage needle hub 26 such that, should a pulling force be applied to needle hub 26 gripping arms 58 exert inward pressure on the needle hub, preventing it from being removed from the sheath. Inward flange 42 is shown engaging outward needle hub flange 60 to prevent rotation of needle hub 26 relative to sheath 10. Only one of the two inward flanges shown in FIG. 9 is visible in FIG. 10 since in FIG. 10 the second outward needle hub flange 60 obscures the second inward flange.

FIG. 11 is a partial axial cross-section view of the sheath structure of FIG. 9, further showing a sterile needle secured to the sheath prior to use. Sheath 10 is shown having break-away connectors 62 attaching the sterile needle to the sheath. As shown, break-away connectors 62 join needle hub 26 to the receiving guide 16 to hold the sterile needle poised for use away from gripping arms 58. Break-away connectors 62 are sufficiently stiff that a syringe may be engaged with annular lip 54 with very little possibility of accidentally pushing the needle hub into gripping arms 58, from which position the sterile needle could not be extracted. However, break-away connectors 62 are sufficiently frangible that they may be compromised by a clockwise rotational force or a lateral pulling action, or a combination thereof, simultaneously removing the needle from the sheath for use. Break-away connectors 62 are equally applicable to the third preferred embodiment discussed above, holding the sterile needle poised away from the needle locking threads ready for use.

FIG. 12 is a partial axial cross-section view of a needle sheath constructed in accordance with the present invention and adapted for disposal of a particular type of needle, namely, a double ended needle having a relatively flat needle hub which engages a needle housing rather than a syringe. Lower needle section 24B is received and contained within sleeve 12' as relatively flat needle hub 26' rotationally engages and is secured by needle hub locking threads 50'. Receiving guide 16' is configured to receive the relatively wide upper needle housing 72. As shown in FIG. 12, receiving guide 16' may be sufficiently large to receive the entire upper needle housing for disposal. Alternatively, upper needle housing 72 may be disconnected from needle hub 26' for separate disposal after needle hub 26' has been secured within sleeve 12 to needle locking threads 50'. In either case, receiving guide 16' encloses upper needle section 24A to prevent accidental contact therewith. Preferably, a locking cap is provided to engage annular ridge 32.

In use, tamper-proof, sealed envelope 40 is opened to access the sterile needle held in sleeve 12. The tamper-proof package cannot be resealed and therefore provides visual evidence of previous opening and, therefore, of sterility. When not included in the kit a syringe is rotationally coupled with the needle hub 26 (See FIG. 2) and both needle 24 and syringe 36 are removed from the sheath by a lateral pulling action. When the tamper-proof package contains a needle secured to the sheath by break-away connectors 62 a rotational and/or twisting motion is used to sever the break-away connectors and remove the needle and syringe. The syringe and sterile needle are then ready for use.

After use, needle 24 is reinserted into sheath 10. The wide aperture of receiving guide 16 provides protection during reinsertion by covering the area of the user's hand gripping sleeve 12 to hold the sheath. The wide aperture also provides a broad target area for reinsertion (See FIG. 4) of the needle. The funnel shape of receiving guide 16 facilitates reinsertion by guiding the needle toward the small open end of receiving guide 16 and, therefore, into the open end of sleeve 12, thereby preventing injury which could otherwise result if the needle were to stray outside the wide aperture.

In the various embodiments of the invention longitudinal or rotational force is applied in inserting the used needle to, alternatively, (i) frictionally engage needle hub 26 with shoulders 28; (ii) frictionally engage needle 24 with tapered frictional surfaces 30; (iii) engage needle hub 26 or outward needle hub flanges 60 with needle hub locking threads 50; or (iv) engage needle hub 26 with gripping arms 58. The syringe is then easily disconnected from needle hub 26 for separate disposal by rotating the syringe relative to the sheath. Rotation of an inserted needle relative to sleeve 12 is prevented by the engagement of inwardly extending flanges 42 with outwardly extending flanges 60 on needle hub 26. Such outwardly extending flanges are provided on needle hubs currently available from Becton Dickinson and Company.

The locking engagement of needle hub 26 with either needle locking threads 50 or gripping arms 58 prevents further removal of the needle from the sheath. Sheath 10, with needle 24 retained in sleeve 12, is preferably sealed by closing cap 18 into the locked position shown in FIG. 3 and is not easily reopened due to the positive, locking engagement of annular ridge 32 with groove 34. These locking measures are particularly important features of the present invention since sheath 10 cannot be reopened and the needle cannot be removed by medical personnel mistakenly believing that the needle contained therein is sterile and ready for use. The locking cap also provides additional protection against accidental dislodging of the used needle from the syringe and prevents accidental opening of the sheath which would allow infectious bacteria to migrate through the environment. Finally, since access to the closed sheath can only be gained by virtually destroying both the sheath and needle, drug abusers cannot easily obtain intact, unsanitary needles. Hinge 20 keeps cap 18 attached to receiving guide 16 in a position ready for closing to assure that the above-mentioned desirable features are not forfeited due to the cap being misplaced.

In the sealed, locked position shown in FIGS. 3 and 7 sheath 10 allows disposal of an unsanitary needle with complete confidence that neither the person reinserting the needle nor any person subsequently handling the sheath will be exposed to injury or infection from either direct contact with or bacteria migrating from the used needle. Since only one needle is disposed of in the novel safety sheath there is no danger of needles piercing or falling out of a cannister, or of bacteria migrating when a cannister is opened to insert additional needles. There is also no danger of drug abusers obtaining intact, unsanitary needles by simply reopening a cannister. The preferred packaging of the sheath with a sterile needle in a tamper-proof envelope (See FIG. 5) provides a convenient method of packaging a sterile needle in close association with a safety disposal sheath constructed in accordance with the present invention.

Advantageously, the sheath according to the present invention can generally be manufactured economically in a single-step, two-part molding process.

To the extent not already indicated, it also will be understood by those of ordinary skill in the art that any one of the various specific embodiments herein described and illustrated may be further modified to incorporate features shown in other of the specific embodiments, as desired.

The invention in its broader aspects therefore is not limited to the specific embodiments herein shown and described but departures may be made therefrom within the scope of the accompanying claims, without departing from the principles of the invention and without sacrificing its chief advantages.

We claim:

1. A disposable safety needle sheath for disposal of a used or otherwise unsanitary needle, comprising:
    sleeve means closed at one end thereof and open at the opposite end thereof;
    needle locking threads within said sleeve means to tightly engage the associated structure of an inserted needle and to effectively prevent a needle inserted into said sleeve means from being readily removed therefrom; and
    needle receiving means communicating with the open end of said sleeve means for guiding a needle inserted therein towards the open end of said sleeve means.

2. The disposable safety needle sheath according to claim 1 wherein said needle locking threads are relatively widely spaced and have steep slope near the juncture of said needle receiving means and said open end of said sleeve and are self-cutting with respect to the associated structure of a needle inserted therein.

3. The dispoable safety needle sheath according to claim 2 wherein said needle locking threads decrease in slope and are more closely spaced distal to said juncture.

4. The disposable safety needle sheath according to claim 2 wherein said needle locking threads stop abruptly and thereafter recommence and gradually attain full thread height.

5. The disposable safety needle sheath according to claim 1 wherein said needle receiving means is integral with the open end of said sleeve means and is configured and dimensioned to enclose the second end of a double-ended needle when the first end of the double-ended needle is inserted into said sleeve means.

6. The disposable needle sheath according to claim 1 wherein said sleeve means, needle retaining means and needle receiving means are all formed from a durable, needle-puncture resistant material.

7. The disposable needle sheath according to claim 1 further comprising a sterile needle mounted partially within said sheath without engaging said needle retaining means.

8. The disposable needle sheath according to claim 7 further comprising break-away mounting braces connecting said sterile needle to said needle sheath.

9. The disposable needle sheath according to claim 7 further comprising a sterile seal encapsulating said sterile sheath and needle.

10. The disposable safety needle sheath according to claim 1 wherein said needle receiving means is funnel-shaped and the small end thereof is integral with the open end of said sleeve means.

11. The disposable safety needle sheath according to claim 1 further comprising a cap assuming a first, open position and a second, closed position effectively sealing the open end of said receiving means.

12. The disposable safety needle sheath according to claim 11 further comprising locking means for preventing said cap from being readily reopened after having assumed said second, closed position.

13. The disposable safety needle sheath according to calim 10 wherein said funnel-shaped needle receiving means has a wide aperture at least twice the diameter of a syringe tip.

14. A disposable safety needle sheath for disposal of a used or otherwise unsanitary needle, comprising:
    sleeve means closed at one end thereof and open at the opposite end thereof for receiving a needle inserted therein;
    needle retaining means within said sleeve means for grasping and holding a needle inserted into said sleeve means, said needle retaining means including one or more relatively stiff needle hub gripping arms extending from the inner wall of said sleeve toward the axis of said sleeve and inclined toward the closed end of said sleeve to effectively prevent a needle inserted into said sleeve from being readily removed therefrom;
    wide aperture needle receiving means communicating with the open end of said sleeve means for guiding a needle inserted into the sheath towards the open end of said sleeve means.

15. The disposable safety needle sheath according to claim 14 wherein said needle hub gripping arms further comprise one or more relatively stiff continuous ridges around the inner circumference of said sleeve.

16. The disposable safety needle sheath according to claim 14 further comprising means for preventing rotation of a needle inserted into said sheath relative thereto.

17. The disposable safety needle sheath according to claim 16 wherein said means for preventing rotation of an inserted needle comprise one or more inwardly projecting flanges integral with said inner sleeve wall whereby said inwardly projecting flanges engage outwardly projecting flanges on a needle hub when a needle is inserted into said sheath.

18. The disposable safety needle sheath according to claim 14 wherein said wide aperture needle receiving means is funnel-shaped and the small end thereof is integral with the open end of said sleeve means.

19. The disposable needle safety sheath according to claim 1 further comprising a cap assuming a first, open position and a second closed position effectively sealing the open end of said receiving means to seal the sheath.

20. The disposable needle safety sheath according to claim 19 further comprising locking means positively engaging said cap and said receiving means to prevent said cap from being readily reopened after assuming said second, closed position.

21. A disposable safety needle sheath for disposal of a used or otherwise unsanitary needle, comprising:
  sleeve means closed at one end thereof and open at the opposite end thereof for receiving a needle inserted therein;
  needle retaining means within said sleeve means for grasping and holding a needle inserted into said sleeve means, said needle retaining means including needle gripping pins extending from the inner wall of said sleeve toward the sleeve axis and angled toward said closed end of said sleeve, and
  wide aperture needle receiving means communicating with the open end of said sleeve means for guiding a needle inserted into the sheath towards the open end of said sleeve means.

22. The disposable safety needle sheath according to claim 16 wherein said relatively stiff annular ridge includes:
  a top slanted surface gradually increasing in diameter relative to the sheath from a first point on said receiving means adjacent to the open end of the sheath to a maximum annular ridge diameter at a point longitudinally displaced away from said open end of the sheath; and
  a bottom surface connecting said maximum annular ridge diameter point to said receiving means at a second point on said receiving means longitudinally displaced away from the sheath opening at a distance not greater than the longitudinal distance from said open end of the sheath to said maximum annular ridge diameter point.

23. The disposable safety needle sheath according to claim 12 wherein said locking means comprise a relatively stiff continuous annular ridge on said wide aperture needle receiving means and a corresponding continuous annular groove in said cap, said cap groove and said annular ridge assuming a first, unlocked position when said cap is in said first, open position and a second, locked position when said cap is in said second, closed position.

24. The disposable safety needle sheath according to claim 22 wherein a portion of said continuous annular groove is in face to face relationship with said annular ridge bottom surface when said annular groove and annular ridge assume said second, locked position, and said stiff annular ridge substantially prevents said annular groove from being removed from said face to face relationship with said annular ridge bottom surface.

25. The disposable safety needle sheath according to claim 24 wherein said face to face relationship lies in a plane perpendicular to the axis of said sleeve means.

* * * * *